(12) United States Patent
Bertram et al.

(10) Patent No.: US 11,877,874 B2
(45) Date of Patent: Jan. 23, 2024

(54) METHOD AND SYSTEM FOR PROJECTING AN INCISION MARKER ONTO A PATIENT

(71) Applicant: Brainlab AG, Munich (DE)

(72) Inventors: Michael Bertram, Markt Schwaben (DE); Florian Glatz, Munich (DE); Georg Christian, Neufahrn (DE)

(73) Assignee: Brainlab AG, Munich (DE)

( * ) Notice: Subject to any disclaimer, the term of this patent is extended or adjusted under 35 U.S.C. 154(b) by 174 days.

(21) Appl. No.: 17/299,635

(22) PCT Filed: Sep. 22, 2020

(86) PCT No.: PCT/EP2020/076357
§ 371 (c)(1),
(2) Date: Jun. 3, 2021

(87) PCT Pub. No.: WO2021/058451
PCT Pub. Date: Apr. 1, 2021

(65) Prior Publication Data
US 2022/0031263 A1    Feb. 3, 2022

(30) Foreign Application Priority Data

Sep. 24, 2019    (WO) .................. PCT/EP2019/075678

(51) Int. Cl.
*A61B 6/04*    (2006.01)
*A61B 6/00*    (2006.01)
*A61B 34/10*    (2016.01)

(52) U.S. Cl.
CPC ............ *A61B 6/0492* (2013.01); *A61B 6/487* (2013.01); *A61B 6/4435* (2013.01); *A61B 2034/107* (2016.02)

(58) Field of Classification Search
CPC ...... A61B 2090/3937; A61B 2034/107; A61B 6/0492; A61B 6/487; A61B 6/08; A61B 6/488; A61B 6/4435
See application file for complete search history.

(56) References Cited

U.S. PATENT DOCUMENTS 9,436,993 B1 *   9/2016  Stolka ................... G06T 5/001
10,159,447 B2 *  12/2018 Klein .................... A61B 6/12
(Continued)

FOREIGN PATENT DOCUMENTS

CN    107468336 A    12/2017
CN    108135563 A    6/2018
(Continued)

OTHER PUBLICATIONS

International Search Report and Written Opinion for corresponding international application No. PCT/EP2020/076357, dated Dec. 3, 2020. 8 pages.

(Continued)

*Primary Examiner* — Dani Fox
*Assistant Examiner* — Soorena Kefayati
(74) *Attorney, Agent, or Firm* — Tucker Ellis LLP

(57) ABSTRACT

This document relates to technologies of projecting an incision marker onto a patient using a movable gantry carrying a medical imaging system and at least one laser which is adjustable relative to the gantry. The medical imaging system is used for capturing a fluoroscopic or x-ray image of at least a part of the patient from a viewing direction. Then a virtual marker is set in the captured image in order to indicate a point or region of interest, for example as a point or at least one line of an incision. Then the laser is used to indicate, from a projection direction different from the viewing direction, the point or region of interest onto the (Continued)

surface of the patient, thus making the point or region of interest visible from the outside.

12 Claims, 3 Drawing Sheets

(56) References Cited

U.S. PATENT DOCUMENTS

| | | | | |
|---|---|---|---|---|
| 2002/0099284 | A1* | 7/2002 | Herrmann | A61B 6/469 |
| | | | | 600/407 |
| 2007/0249967 | A1* | 10/2007 | Buly | A61B 5/1121 |
| | | | | 600/595 |
| 2008/0243142 | A1* | 10/2008 | Gildenberg | G16H 30/40 |
| | | | | 606/130 |
| 2013/0345718 | A1* | 12/2013 | Crawford | A61B 17/8866 |
| | | | | 606/130 |
| 2015/0297151 | A1* | 10/2015 | Florent | A61B 6/5205 |
| | | | | 600/424 |
| 2015/0366624 | A1* | 12/2015 | Kostrzewski | A61B 34/76 |
| | | | | 606/130 |
| 2016/0048960 | A1* | 2/2016 | Zino | G06T 15/08 |
| | | | | 382/128 |
| 2017/0116729 | A1* | 4/2017 | Stolka | G06V 20/52 |
| 2017/0172669 | A1* | 6/2017 | Berkowitz | A61B 90/96 |
| 2017/0209110 | A1* | 7/2017 | Kiraly | A61B 6/44 |
| 2017/0224298 | A1* | 8/2017 | Hannemann | A61B 6/469 |
| 2017/0348061 | A1* | 12/2017 | Joshi | A61B 90/90 |
| 2018/0116731 | A1* | 5/2018 | State | A61B 17/07207 |
| 2018/0150960 | A1* | 5/2018 | Derda | G06T 7/0012 |
| 2018/0206809 | A1* | 7/2018 | Sato | A61B 6/503 |
| 2019/0015056 | A1* | 1/2019 | Sato | A61B 6/487 |
| 2019/0076195 | A1* | 3/2019 | Shalayev | A61B 34/10 |
| 2019/0184200 | A1* | 6/2019 | Mori | A61N 5/1049 |
| 2019/0209080 | A1* | 7/2019 | Gullotti | A61B 17/7035 |
| 2019/0350657 | A1* | 11/2019 | Tolkowsky | A61B 46/20 |
| 2020/0078097 | A1* | 3/2020 | Gregerson | A61B 5/1127 |
| 2020/0159313 | A1* | 5/2020 | Gibby | G06T 7/33 |
| 2020/0268339 | A1* | 8/2020 | Hao | G06T 7/0014 |
| 2020/0405399 | A1* | 12/2020 | Steinberg | G06N 20/00 |

FOREIGN PATENT DOCUMENTS

| | | |
|---|---|---|
| CN | 108836509 A | 11/2018 |
| DE | 10057027 A1 | 6/2002 |
| EP | 3254627 A1 | 12/2017 |
| WO | 00/64223 A2 | 10/2000 |
| WO | 2017/083017 A1 | 5/2017 |

OTHER PUBLICATIONS

Office Action received in corresponding CN case, application No. 202080006509.0, dated Nov. 23, 2023, 11 pages.

Search Report received in corresponding CN case, application No. 202080006509.0, dated Nov. 23, 2023, 1 page.

* cited by examiner

US 11,877,874 B2

METHOD AND SYSTEM FOR PROJECTING AN INCISION MARKER ONTO A PATIENT

RELATED APPLICATION DATA

This application is a National Phase application of International Application No. PCT/EP2020/076357, filed Sep. 22, 2020, which claims priority to International Application No. PCT/EP2019/075678, filed on Sep. 24, 2019, the contents of both of which are incorporated herein by reference.

FIELD OF THE INVENTION

The present invention relates to a method for projecting an incision marker onto a patient, a corresponding computer program, a program storage medium storing such a program and a computer for executing the program, as well as a medical system comprising the aforementioned computer.

TECHNICAL BACKGROUND

Medical imaging systems for obtaining fluoroscopic or x-ray images are typically used for planning surgeries or for verification of information immediately before surgery. In this document, the functionality of such a medical imaging system is extended by adding the capability of projecting an incision marker onto a patient.

The medical imaging system typically comprises an x-ray source which emits a conical x-ray beam, which can optionally be shaped using a collimator. The medical imaging system further typically comprising a two-dimensional x-ray detector for detecting the x-ray beam after it has passed the patient. With such a medical imaging system, a two-dimensional fluoroscopic image can be captured. However, it is also possible that the medical imaging system comprises an x-ray source emitting a fan-shaped x-ray beam and a line x-ray detector corresponding to the fan-shaped x-ray beam. Such an imaging system captures a one-dimensional x-ray image, but a two-dimensional fluoroscopic image can be obtained by moving the medical image system relative to the patient and combining a plurality of one-dimensional x-ray images. The center of the x-ray beam is also referred to as the central beam of the medical imaging system.

The present invention can be used for preparational procedures e.g. in connection with a medical imaging system such as Loop-X™, which is a product of Brainlab AG, or any other suitable imaging system.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

This document relates to technologies of projecting an incision marker onto a patient using a movable gantry carrying a medical imaging system and at least one laser which is adjustable relative to the gantry. The medical imaging system is used for capturing a fluoroscopic or x-ray image of at least a part of the patient. Then a virtual marker is set in the captured image in order to indicate a point or region of interest, for example as a point or at least one line of an incision. Then the laser is used to indicate the point or region of interest onto the surface of the patient, thus making the point or region of interest visible from the outside.

GENERAL DESCRIPTION OF THE INVENTION

In this section, a description of the general features of the present invention is given for example by referring to possible embodiments of the invention.

In general, the invention reaches the aforementioned object by providing, in a first aspect, a method of projecting an incision marker onto a patient using a medical imaging system comprising a gantry and at least one laser which is adjustable relative to the gantry.

The method comprises a step of capturing a fluoroscopic image of at least a part of the patient, in particular of at least a part of a patient's bony structure, e.g. of the spine of the patient. The medical imaging system is capable of capturing the fluoroscopic image and therefore comprises, for example, an x-ray source and x-ray detector. In one embodiment, only a single fluoroscopic image is captured. The fluoroscopic image is then displayed on a display device.

The fluoroscopic image is taken from a viewing direction onto the patient which represents the position of the medical imaging system relative to the patient. The viewing direction for example represents the direction of a line defined relative to the medical imaging system, such as the line which coincides with the centre of the x-ray beam emitted by the x-ray source.

The method further comprises the step of setting a virtual marker in the fluoroscopic image. This virtual marker for example indicates a point or region of interest, such as a point or region to be treated by surgery or indicating a position of an incision.

The method further involves the step of controlling the at least one laser to project the incision marker in accordance with the virtual marker onto the patient from a projection direction different from the viewing direction. In other words, the incision marker projected onto the patient indicates a position on the surface of the patient which corresponds to the position of the virtual marker in the fluoroscopic image.

In this document, the word "laser" refers to an apparatus which generates a laser beam. This beam can have different shapes, such as a point shape, such that the laser beam is a straight line, or a fan shape, such that the laser beam covers a section of a plane with a particular opening angle. This opening angle defines the angle between the two boundary lines of the laser beam.

The projection direction is the direction from which the incision marker is projected onto the patient. If the incision marker is a single spot, then the projection direction typically equals the direction of the laser beam. If the laser is fanned out to project a line onto the patient, the projection direction is for example the central axis of the fan. If the incision marker comprises two intersecting lines, such as a crosshair, the projection direction is for example the line which connect the intersection with the origin of the laser beam, like the laser source or a deflecting mirror.

In one embodiment, the angle between viewing direction and the projection direction is 90°, between 85° and 95°, between 80° and 100° or between 70° and 110°.

If for example the viewing direction is a lateral direction of the patient, such that the fluoroscopic image is taken from a lateral side of the patient, the incision marker is for example projected onto the rear side or the front side of the patient.

The laser is for example calibrated with the medical imaging system. This means that the position of the laser relative to the medical imaging system is known, which means that the position of the laser beam can be adjusted relative to the medical imaging system. This calibration can for example be obtained using a phantom or a back projection. If the orientation of the laser relative to the imaging system is known, the orientation of the laser is also known relative to the imaging plane.

The present method has the advantage that a point or region of interest can be marked in an image of the patient, which allows a look into the patient, and a position corresponding to the point or region of interest can then be indicated on the surface of the patient from a different direction. This has the advantage that no additional tools such as markers and no repeated irradiation is necessary and the incision marker can be set in an image showing details of the imaged part of the patient which might not be recognizable in an image taken from the projection direction.

Since the viewing direction of the medical imaging system when capturing the fluoroscopic image is known, the position of the imaging plane of the image detector, and thus the position of the fluoroscopic image, in a reference system of the medical imaging system is known. The position of the incision marker is then also defined in the reference system of the medical imaging system. This means that there is no need to track or register the patient as long as the patient has the same position relative to the medical imaging system both at capturing the fluoroscopic image and projecting the incision marker.

In one application, the fluoroscopic image shows at least a part of the patient's spine, one vertebra or a plurality of vertebrae can be marked in the fluoroscopic image and the position of the selected vertebra or vertebrae inside the patient can be indicated by the incision markers. From the outside, the position of vertebra cannot be sensed directly, only in some cases the position of a spinous process, in some cases it is impossible to sense a part of the spine directly, e.g. for obese patients. However, there is no universal correlation between the position of the vertebra and its spinous process, so the actual position of the vertebra cannot be ascertained. This is solved by the present invention.

In one embodiment, the at least one laser projects an imaging marker onto the patient, wherein the imaging marker indicates the image position on the patient when the fluoroscopic image is captured. The imaging marker for example represents the central beam of the x-ray source. In other words, the imaging marker can be used for positioning the medical imaging system relative to the patient such that the patient is positioned correctly within the field of view of the medical imaging system. In the present embodiment, the same laser can be used for projecting an imaging marker and, later on, an incision marker.

In one embodiment, an initial virtual marker is overlaid over the fluoroscopic image, wherein the position of the initial virtual marker corresponds to the position of the imaging marker on the patient. This means that the imaging direction of the medical imaging system when capturing the fluoroscopic image is indicated in the fluoroscopic image. If the imaging marker indicates the central beam of the x-ray source, then the initial virtual marker indicates the position of the central beam in the fluoroscopic image. The initial virtual marker for example indicates the longitudinal position of the imaging marker on the patient in the fluoroscopic image.

In one embodiment, the method further comprises the step of changing the position of the initial virtual marker to obtain the virtual marker. The position is for example changed according to user input data, which represents the intended movement of the initial virtual marker. It can also be said that the initial virtual marker becomes the virtual marker once it is overlaid over the fluoroscopic image and the incision marker is projected according to the position of the virtual marker. Setting the virtual marker thus includes moving the initial virtual marker.

In general, setting the virtual marker can be performed by moving, for example dragging, of the virtual marker in the fluoroscopic image. It can further be performed by clicking on a point in the fluoroscopic image.

In another embodiment, the virtual marker can be set by indicating a structure, for example by selecting a structure from one or more list(s) of structures. It is for example possible to indicate a structure like a landmark of a bone. This structure is then automatically found in the fluoroscopic image and the virtual marker is set accordingly. In another example, a list of bones shown in the fluoroscopic image is displayed and a user selects one of the bones. In an optional second step, a list of landmarks and/or sections of the selected bone is displayed and the user selects a landmark or section to which the virtual marker is then automatically set. The automatically set virtual marker can then be modified by the user.

In the above, a user making a selection involves receiving user input indicating the selection.

In one embodiment, controlling the at least one laser involves at least one of performing a linear displacement of the at least one laser in one translational dimension and performing a rotational displacement of laser beam emitted by the at least one laser about one axis. In one example, the linear/or rotational displacement is relative to the gantry. The rotational displacement of the laser beam can for example be achieved using a mirror which is adjustable to modify the direction of the laser beam. The one axis about which the laser beam is displaced is for example orthogonal to the direction of the laser beam or lies in the plane in which the laser beam lies.

With the displacement relative to the gantry it is possible to project the incision marker to the correct position without the need to move the gantry relative to the patient.

In another implementation, controlling the at least one laser to project the incision marker involves a rotation of the laser, for example about the vertical axis of the patient.

The vertical axis is also called craniocaudal or longitudinal axis. In one embodiment, the laser moves on a circular trajectory. The laser can for example move relative to the gantry, for example inside the gantry, for example on a rail. The laser can for example move together with the x-ray detector. If the laser is rigidly attached to the gantry, the gantry, or a part of the gantry which carries the laser, performs the rotation. The rotation of the laser is in particular useful if the laser used for projecting an imaging marker is also used for projecting an incision marker since the projection of the incision marker is to be made from a direction which differs from the imaging direction of the fluoroscopic image.

In one implementation, the laser is attached to the x-ray detector. Positioning the laser source such that the incision marker can be projected from the projection direction then optionally involves rotating the x-ray detector about the patient, for example about the longitudinal axis of the patient, for example together with or along the gantry. The rotation of the x-ray detector, starting from the position in which the x-ray detector is used for capturing the fluoroscopic image, is then for example 90°, between 85° and 95°, between 80° and 100° or between 70° and 110°. The laser being attached to the x-ray detector can mean a rigid attachment or an attachment in which the laser is movable relative to the x-ray detector, for example along a rail.

In one embodiment, the virtual marker is a point. Such a point can for example mark a single object within the patient. The point can be initially set, for example using a graphical user interface, or can be an existing point which is moved within the fluoroscopic image. The existing point can for example indicate the central beam of the medical imaging system when the fluoroscopic image was captured as explained above. The point can also be marked by a crosshair.

In this embodiment, the at least one laser for example projects a point or crosshair as the incision marker. The point or crosshair can for example mark a point suitable for an incision or a minimal invasive cut for reaching the point indicated by the virtual marker.

In one embodiment, the virtual marker indicates a vertical position of the spine. The vertical position means the position along the longitudinal axis of the patient. The virtual marker can for example indicate the start or the end of a desired incision which is to be indicated by the incision marker.

In one implementation, the beam emitted by the at least one laser points in an anterior-posterior direction of the patient. The laser beam is for example projected onto the back of the patient and can thus indicate the vertical position on the spine represented by the virtual marker.

In one implementation, the laser projects a line as the incision marker. This line for example lies in the horizontal plane of the patient, which is also referred to as the transverse plane.

The line can for example be obtained by fanning out a point beam, for example using an optical prism or by scanning the laser beam, for example using a movable mirror.

In one embodiment, the method further comprises the step of setting a second virtual marker in the fluoroscopic image. In one case, the first virtual marker indicates a first end of the desired incision and the second virtual marker indicates a second end of the desired incision. However, it is possible to use the second virtual marker for any point of region of interest. In this embodiment, another step is controlling the at least one laser to project a second incision marker in accordance with the second virtual marker. This means that two incision markers are projected corresponding to two virtual markers. It is, however, also possible to set three or more virtual markers resulting in three or more incision markers projected by the at least one laser.

The second incision marker can be projected by the same laser which projects the first incision marker, for example by using a mirror for deflecting the laser beam. However, it is also possible to use a different laser for projecting the second incision marker.

In one embodiment, the method further comprises the steps of changing the position of the virtual marker in the fluoroscopic image and of controlling the at least one laser according to the changed position of the virtual marker to adapt the position of the corresponding incision marker in real time. This means that the position of a virtual marker can be adjusted in the fluoroscopic image and the effect of the changed position of the virtual marker can immediately be visualized on the surface of the patient.

The present invention also refers to a program which, when running on a computer that is connected to a medical imaging system comprising a movable gantry and at least one laser which is adjustable relative to the gantry, causes the computer to perform the steps of acquiring a fluoroscopic image of at least a part of the spine of a patient, receiving user input representing a virtual marker in the fluoroscopic image and outputting control parameters for controlling the at least one laser to project an incision marker onto the patient in accordance with the virtual marker.

The program corresponds to the method described above, and therefore achieves the same technical effects, but relates to mere data processing aspects.

The present invention further relates to a computer on which the aforementioned program is stored and/or run.

The present invention further relates to a system comprising said computer and a medical imaging system comprising a gantry and at least one laser which is adjustable relative to the gantry.

Still further, the present invention relates to a non-transitory computer readable storage medium on which said program is stored.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of performing an incision. More particularly, the invention does not involve or in particular comprise or encompass any surgical or therapeutic activity. The invention is instead directed as applicable to preparation of an incision. For this preparation alone, no surgical or therapeutic activity and in particular no surgical or therapeutic step is necessitated or implied by carrying out the invention. The incision markers can rather, for example, be used as a marker at which a person draws a mark on the skin of the patient using a pen or the like.

Use of the Device or System

The present invention also relates to the use of the device/system or any embodiment thereof for projecting an incision marker onto a patient.

Definitions

In this section, definitions for specific terminology used in this disclosure are offered which also form part of the present disclosure.

Computer Implemented Method

The method in accordance with the invention is for example a computer implemented method for performing the method steps or instructing an entity to perform a method step as appropriate. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp)

and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device).

Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Landmarks

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the center of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational center of the femur when moved relative to the acetabulum.

BRIEF DESCRIPTION OF THE DRAWINGS

In the following, the invention is described with reference to the appended figures which give background explanations and represent specific embodiments of the invention.

The scope of the invention is however not limited to the specific features disclosed in the context of the figures, wherein.

DESCRIPTION OF EMBODIMENTS

Figure 1:
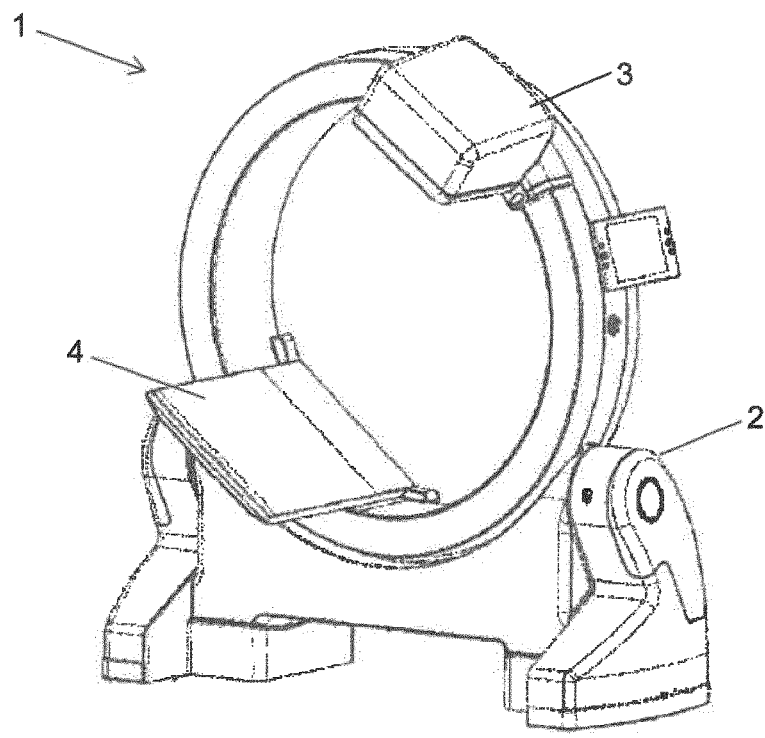
FIG. 1 illustrates a medical imaging system.

FIG. 1 schematically shows a medical imaging system 1 comprising a gantry 2 carrying an x-ray source 3 and carrying an x-ray detector 4. The gantry 2 comprises a base and a ring, wherein at least the x-ray detector 4, but optionally also the x-ray source 3, is rotatable in the ring. The base 2 comprises wheels (not shown) with which the medical imaging system 1 can be positioned, for example in an operating room. The ring might be tiltable relative to the base.

The x-ray source 3 emits x-ray beam which radiographs a patient (not shown) and is then detected using the detector 4 and converted into a displayable image which is recognizable by a human being.

Figure 2:
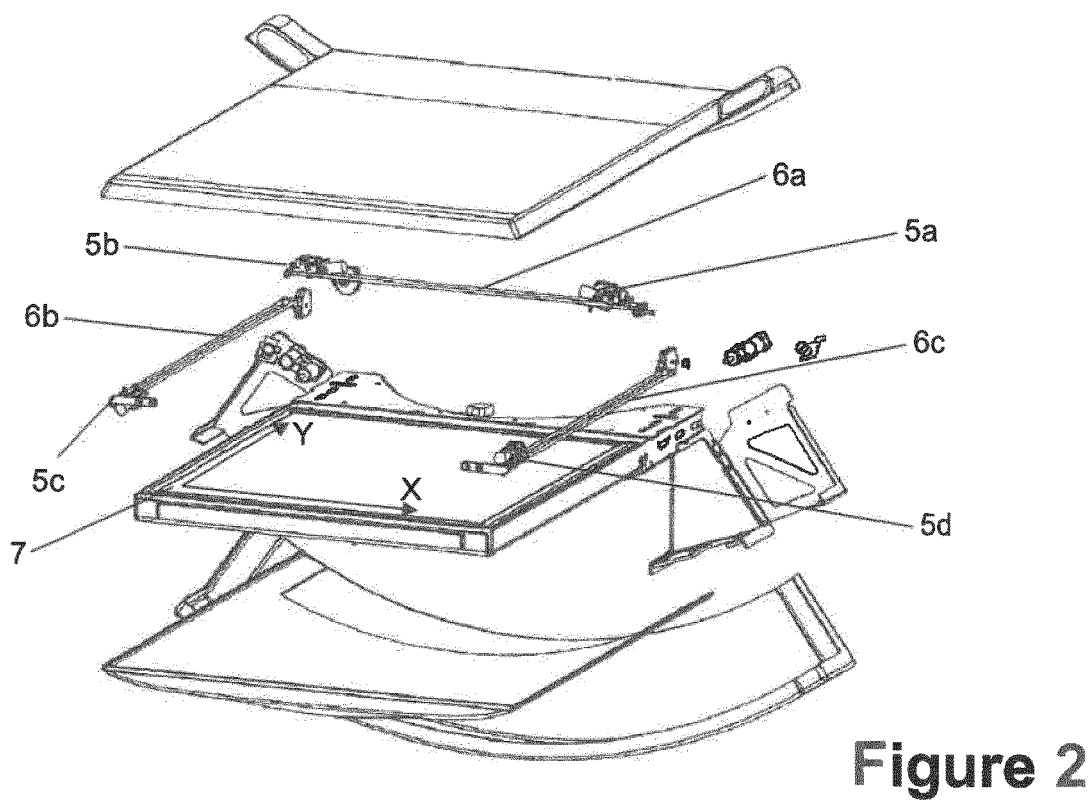
FIG. 2 shows details of the detector including lasers.

FIG. 2 shows an exploded view of the x-ray detector 4. It comprises a detector panel 7 which is two-dimensional defined by an X direction and an Y direction which are orthogonal to each other. Adjacent to the detector panel 7, there are guide rails 6a, 6b and 6c, wherein guide rail 6a carries lasers 5a and 5b, guide rail 6b carries laser 5c and guide rail 6c carries laser 5d. Each laser 5 emits a laser beam. In the present embodiment, each laser beam is a fan beam lying in a particular plane. This plane is typically perpendicular to the direction in which the corresponding guide rail 6 extends. This means that the fan beam emitted by the lasers 5a and 5b typically lies in a plane spanned by the Y direction and a Z direction perpendicular to both the Y direction and the X direction, and the laser beams emitted by the lasers 5c and 5d typically lie in a plane spanned by the X direction and Z direction. However, in the present embodiment, the laser beams can be tilted relative to said planes, for example using a pivotable mirror. The laser beams emitted by the lasers 5a and 5b can be rotated about the Y direction and the beams emitted by the lasers 5c and 5d can be rotated about the X direction.

When capturing a fluoroscopic image using the medical imaging system 1, the lasers 5 can be used to indicate the field of view of the medical imaging system. In one embodiment, two lasers project a crosshair indicating the central beam of the medical imaging system 1. In another embodiments, the lasers 5 are controlled to emit their beams towards the x-ray source 3, such that the beams indicate the boundaries of the x-ray beam.

Figure 3:
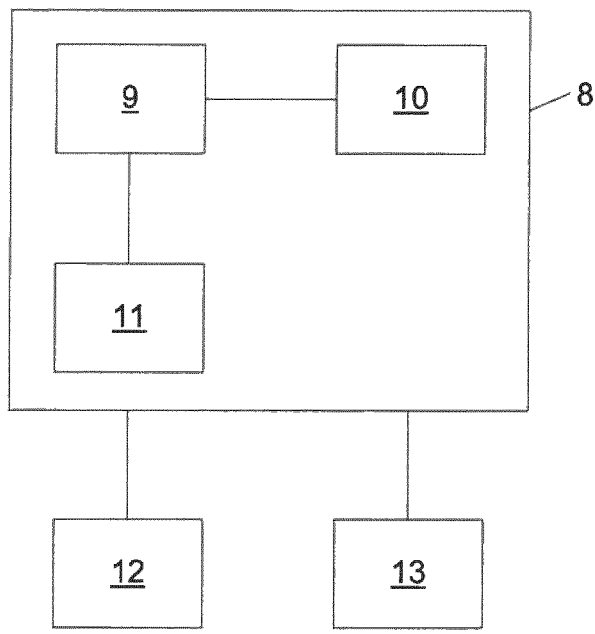
FIG. 3 is a schematic illustration of a computer for implementing the method.

FIG. 3 schematically shows a computer 8 connectable to the medical imaging system 1. The computer 8 comprises a central processing unit 9, a memory 10 and an interface 11 for connecting the computer 8 to the medical imaging system 1. The computer 8 is connected to an input device 12 such as a keyboard and/or a mouse, and an output device 13, such as a monitor. The memory 10 stores instructions which, when carried out by the central processing unit 9, implement the claimed method. The memory 10 may further store working data, such as a fluoroscopic image obtained from the medical imaging system 1. The computer 8 is further configured to control the imaging device 1 via the interface 11, for example to control one or more of the lasers 5 or to activate actuators of the medical imaging system, for example for moving the base of the gantry 2 or rotating the x-ray source and/or the x-ray detector 4 within the ring of the gantry 2.

Figure 4:
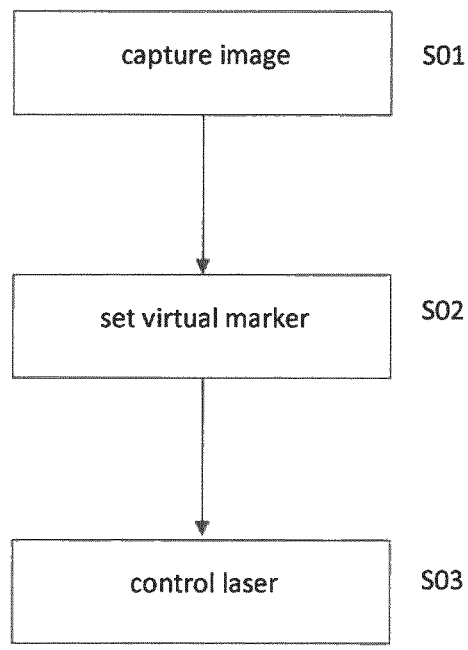
FIG. 4 shows a workflow of the method.

FIG. 4 shows the general structure of the claimed method.

Step S01 involves capturing an image of at least a part of a patient using the medical imaging system 1. The fluoroscopic image is transferred to the computer 8 and displayed on the output device 13. Using the input device 12, a user can set one or more virtual markers in the fluoroscopic image in step S02.

In step S03, the computer 8 controls at least one of the lasers 5 to project an incision marker in accordance with the virtual markers set in step S02.

Figure 5A:
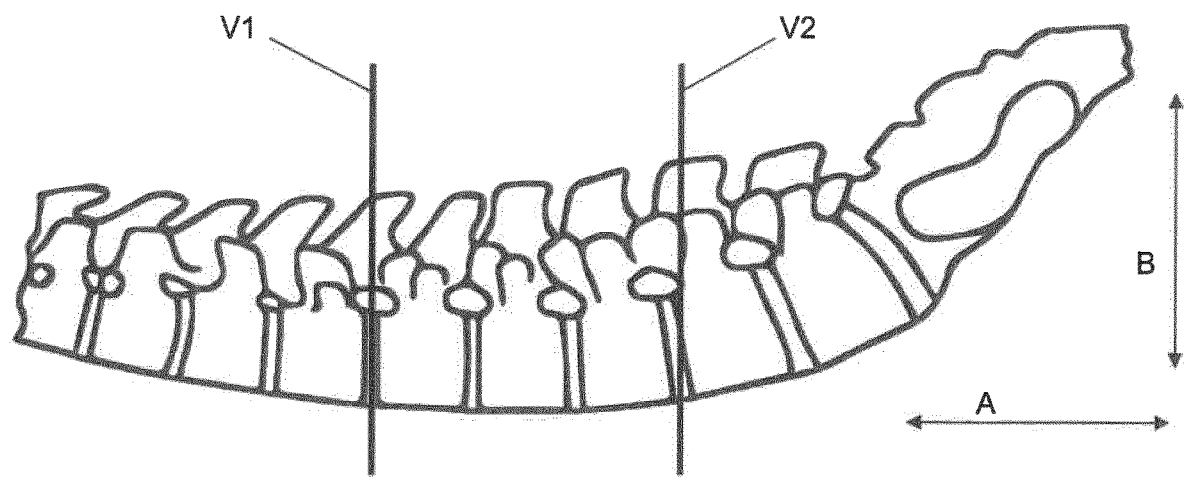
FIG. 5a shows a fluoroscopic image with two virtual markers.

FIG. 5a shows an exemplary lateral fluoroscopic image of a part of the spine of a patient taken from a lateral direction. Arrow A indicates the longitudinal direction of the patient and Arrow B indicates the anterior-posterior direction of the patient. The lateral direction is perpendicular both to the longitudinal direction and the anterior-posterior direction.

In the example of FIG. 5a, two virtual markers V1 and V2 in terms of vertical lines are set in the lateral fluoroscopic image. The two virtual markers V1 and V2 mark the beginning and the end of a region extending in the longitudinal direction of the patient which shall be accessed by an incision. It shall be noted that the two end points could also be indicated by virtual markers in the shape of points or any other suitable shape.

Figure 5B:
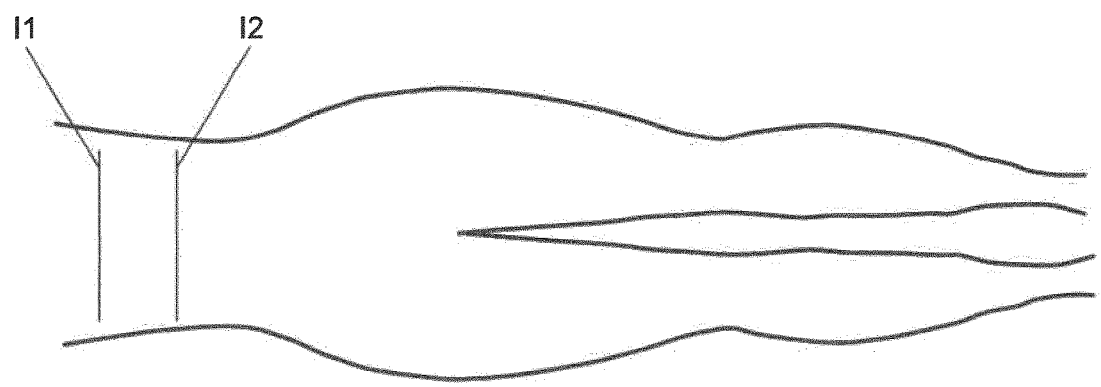
FIG. 5b shows a side view of the patient with two incision markers.

In the example shown in FIG. 5a, the computer 8 controls the lasers 5a and 5b to project two parallel lines onto the back of the patient corresponding to the positions of the virtual markers V1 and V2 in the fluoroscopic image. The two parallel lines are shown as incision markers 11 and 12 in FIG. 5b, which is a schematic rear view of the patient. The incision markers can have other shapes, such as points, dots, crosshairs or any other suitable shape. If necessary, the computer 8 instructs the medical navigation system to rotate the ring of the gantry 2 together with the x-ray detector 4, or the x-ray detector 4 along the gantry 2, such that the lasers 5A and 5B are in a position from which they can emit their laser beams onto the back of the patient. It is possible to project only one or more than two incision markers onto the back, or rear side, of the patient, based on the position of a corresponding number of virtual markers set in the lateral fluoroscopic image.

Since the viewing direction of the fluoroscopic image onto the patient is known (in this case, the lateral direction), and the lasers 5 are calibrated with respect to the gantry 2, the computer 8 can calculate the position of the lasers 5 along the guide rails 6 and the angle at which the lasers must emit the laser beams such that the laser lines are projected onto the correct positions on the surface of a patient.

In a modification or extension of the embodiments, it is possible to move a virtual marker V1 or V2 in the corresponding fluoroscopic image using the input device 12. If the position of the virtual marker in the fluoroscopic image is changed, the computer 8 instructs the lasers 5 in real time to adapt the positions of the laser lines of the surface of the patient.

The invention claimed is:

1. A method of projecting an incision marker onto a patient using an associated medical imaging system comprising a gantry and at least one laser that is adjustable relative to the gantry, the method comprising:

capturing a fluoroscopic image of at least a part of a bony structure of the patient from a viewing direction onto the patient using the associated medical imaging system;

projecting, by the at least one laser, an imaging marker onto the patient, wherein the imaging marker indicates a position of the fluoroscopic image on the patient when the fluoroscopic image is captured;

overlaying an initial virtual marker over the fluoroscopic image, wherein a position of the initial virtual marker in the fluoroscopic image corresponds with a position of the imaging marker projected onto the patient;

setting a virtual marker in the fluoroscopic image; and controlling the at least one laser to project the incision marker in accordance with the virtual marker onto the patient from a projection direction different from the viewing direction.

2. The method of claim 1, wherein an angle between the viewing direction and the projection direction lies between 85° and 95°.

3. The method of claim 1, further comprising changing the position of the initial virtual marker to obtain the virtual marker.

4. The method of claim 1, wherein the virtual marker comprises a point.

5. The method of claim 1, wherein:
the capturing the fluoroscopic image of the at least a part of the bony structure of the patient comprises capturing a fluoroscopic image of at least a part of a spine of the patient; and
the setting the virtual marker comprises setting the virtual marker that indicates a vertical position on the spine.

6. The method of claim 1, further comprising:
setting a second virtual marker in the fluoroscopic image; and
controlling the at least one laser to project a second incision marker in accordance with the second virtual marker.

7. The method of claim 1, further comprising:
changing the position of the virtual marker in the fluoroscopic image; and
controlling the at least one laser according to the changed position of the virtual marker to adapt the position of the corresponding incision marker in real time.

8. The method of claim 4, wherein the at least one laser projects a point or a crosshair as the incision marker.

9. The method of claim 5, wherein the projecting by the laser comprises projecting a line as the incision marker.

10. A non-transitory computer readable storage medium storing a program that, when running on a computer that is connected with an associated medical imaging system comprising a gantry and at least one laser that is adjustable relative to the gantry, causes the computer to perform steps comprising:

acquiring a fluoroscopic image of at least a part of a bony structure of a patient from a viewing direction onto a patient using the associated medical imaging system;

instructing the at least one laser to project an imaging marker onto the patient, wherein the imaging marker indicates a position of the fluoroscopic image on the patient when the fluoroscopic image is captured;

overlaying an initial virtual marker over the fluoroscopic image, wherein a position of the initial virtual marker in the fluoroscopic image corresponds with a position of the imaging marker projected onto the patient;

receiving a user input representing a virtual marker in the fluoroscopic image; and outputting control parameters for controlling the at least one laser to project an incision marker onto the patient in accordance with the virtual marker from a projection direction different from the viewing direction.

11. A computer comprising a processor and a non-transitory computer readable storage medium storing a program executable by the processor to:

control an associated medical imaging system comprising a gantry and at least one laser that is adjustable relative to the gantry to capture a fluoroscopic image of at least a part of a bony structure of an associated patient from a viewing direction onto the associated patient;

control the at least one laser to project an imaging marker onto the patient, wherein the imaging marker indicates a position of the fluoroscopic image on the patient when the fluoroscopic image is captured;

control the associated medical imaging system to overlay an initial virtual marker over the fluoroscopic image, wherein a position of the initial virtual marker in the fluoroscopic image corresponds with a position of the imaging marker projected onto the patient;

control the associated medical imaging system to set a virtual marker in the fluoroscopic image; and control the at least one laser to project the incision marker in accordance with the virtual marker onto the associated patient from a projection direction different from the viewing direction.

12. A system comprising:
a medical imaging system comprising a gantry and at least one laser that is adjustable relative to the gantry; and
a computer comprising:
a processor; and
a non-transitory computer readable storage medium storing a program executable by the processor to:
control the medical imaging system to capture a fluoroscopic image of at least a part of a bony structure of an associated patient from a viewing direction onto the associated patient;
control the at least one laser to project an imaging marker onto the patient, wherein the imaging marker indicates a position of the fluoroscopic image on the patient when the fluoroscopic image is captured;
control the medical imaging system to overlay an initial virtual marker over the fluoroscopic image, wherein a position of the initial virtual marker in the fluoroscopic image corresponds with a position of the imaging marker projected onto the patient;
control the medical imaging system to set a virtual marker in the fluoroscopic image; and
control the at least one laser to project the incision marker in accordance with the virtual marker onto the associated patient from a projection direction different from the viewing direction.

* * * * *